(12) United States Patent
Bickel

(10) Patent No.: US 6,253,916 B1
(45) Date of Patent: Jul. 3, 2001

(54) SHARPS DISPOSAL ASSEMBLY HAVING IMPROVED UNWINDER

(76) Inventor: Christopher R. Bickel, 52 Jacksonville Dr., Parsippany, NJ (US) 07054

( * ) Notice: Subject to any disclaimer, the term of this patent is extended or adjusted under 35 U.S.C. 154(b) by 0 days.

(21) Appl. No.: 09/559,043

(22) Filed: Apr. 27, 2000

(51) Int. Cl.⁷ .................................................. B65D 83/10
(52) U.S. Cl. ........................................... 206/366; 206/370
(58) Field of Search .................................... 206/363–366, 206/370; 220/908; 588/249, 258; 604/110

(56) References Cited

U.S. PATENT DOCUMENTS

| | | | |
|---|---|---|---|
| 4,375,849 | 3/1983 | Hanifl . | |
| 4,466,538 | * 8/1984 | Gianni | 206/370 |
| 4,875,265 | * 10/1989 | Yoshida | 206/366 |
| 4,892,191 | * 1/1990 | Nakamura | 206/366 |
| 5,092,462 | 3/1992 | Sagstetter et al. . | |
| 5,183,156 | * 2/1993 | Bruno | 206/366 |
| 5,275,280 | * 1/1994 | Everhart | 206/366 |
| 5,322,164 | * 6/1994 | Richardson et al. | 206/366 |
| 5,402,887 | * 4/1995 | Shillington | 206/370 |
| 5,415,315 | 5/1995 | Ramirez . | |
| 5,573,113 | * 11/1996 | Shillington et al. | 206/366 |

* cited by examiner

Primary Examiner—Luan K. Bui
(74) Attorney, Agent, or Firm—Richard E. Brown

(57) ABSTRACT

A sharp disposal assembly includes a receptacle, lid therefor and an unwinder having three flanges on each side of a slot opening in the lid. A substantially cubical compartment formed by the six flanges receives a needle-hub-safety shield unit in a loose non-binding immobilization which provides firm support to the unit during unwinding and yet precludes any hangup which might necessitate manual separation.

8 Claims, 5 Drawing Sheets

SHARPS DISPOSAL ASSEMBLY HAVING IMPROVED UNWINDER

FIELD OF THE INVENTION

This invention relates to medical devices and more particularly relates to blood sampling devices and safe disposal thereof.

BACKGROUND OF THE INVENTION

Many medical articles used in hospitals and clinics are designed for one-time use. Articles which have sharp points, cutting edges and the like, are collectively known as sharps, and many disclosures of special equipment and procedures have been proposed to minimize the danger of injury such as needle sticks, to personnel involved in the use or disposal of these articles. Safe handling and disposal is particularly important, since a sharp is often used in a procedure, such as blood sampling, and as a result may be contaminated with a potentially infectious agent.

Many designs of disposal equipment for sharps have been proposed. Most include a storage container having a lid with locking closure features and several openings through the lid for access to the interior of the container. Often the sharp is affixed to a hub having threads mated to a tube holder, and it is conventional that one of the openings have structure associated therewith, known as the unwinder, for unthreading the sharp from the holder without any manual manipulation by the user.

Conventional unwinders operate by inserting a needle-hub member into the large end of a V-shaped opening and advancing the member toward the narrow end of the opening until ribs on the hub engage the wall of the unwinder. At this point, a twisting rotation of the needle holder causes the hub-needle member to drop off into the container. A common problem encountered with this design is hangup of the hub on the wall after removal of the holder, and occurs when the hub has engaged the wall too strongly. Typical sharps containers having an unwinder designed to unthread needle-hub members are disclosed in U.S. Pat. No. 4,375,849 to Hanifl and U.S. Pat. No. 5,415,315 to Ramiriz et al. respectively. An unwinder for double-ended needles is disclosed in U.S. Pat. No. 5,092,462 to Sagstetter et al.

While the above disclosures have advanced the art of sharps disposal, prior art unwinders do not perform well for disposal of sharps protected by a modern safety shield which prevents the unwinder from grasping the ribs. Thus, if a needle-hub-shield unit is advanced in a conventional unwinder, the shield must be tightly wedged between the opposite walls of the unwinder, often leading to severe hangup. Further, many reports from field use have described inadvertent premature raising-up of the holder by the technician before complete disengagement of the hub threads from the holder threads, a common occurrence also causing holdup and failure of the sharp to drop into the container. The present invention is directed to an unwinder design directed to overcoming these problems.

SUMMARY OF THE INVENTION

A sharps disposal assembly includes a receptacle, a lid for the receptacle and an unwinder having features for separating a needle-hub-member, preferably a needle-hub-safety shield unit, from a needle holder. The unwinder includes a slot or V-shaped opening bounded by an edge having flanges integral thereto which, along with a wedge-shaped segment of the lid, form a compartment in the opening which receives the safety shield in a loose non-binding fit. The assembly includes a large port opening for receiving large items such as blood collection sets, syringes and needle holders and the like. Preferred assemblies include closure flaps to cover the openings.

Because the unwinder defines a substantially cubical compartment loosely enclosing a conventional needle shield on three sides and the top, wedging cannot take place either during twisting or inadvertent pull-up, and no hangup can occur.

DETAILED DESCRIPTION

While this invention is satisfied by embodiments in many different forms, there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

The following description is directed to the preferred embodiment of the invention wherein the assembly is used to unwind threaded components, one of which is protected by a conventional needle shield, with the understanding that the new unwinder design may be used to disengage threads on any medical article to be discarded.

Figure 1:
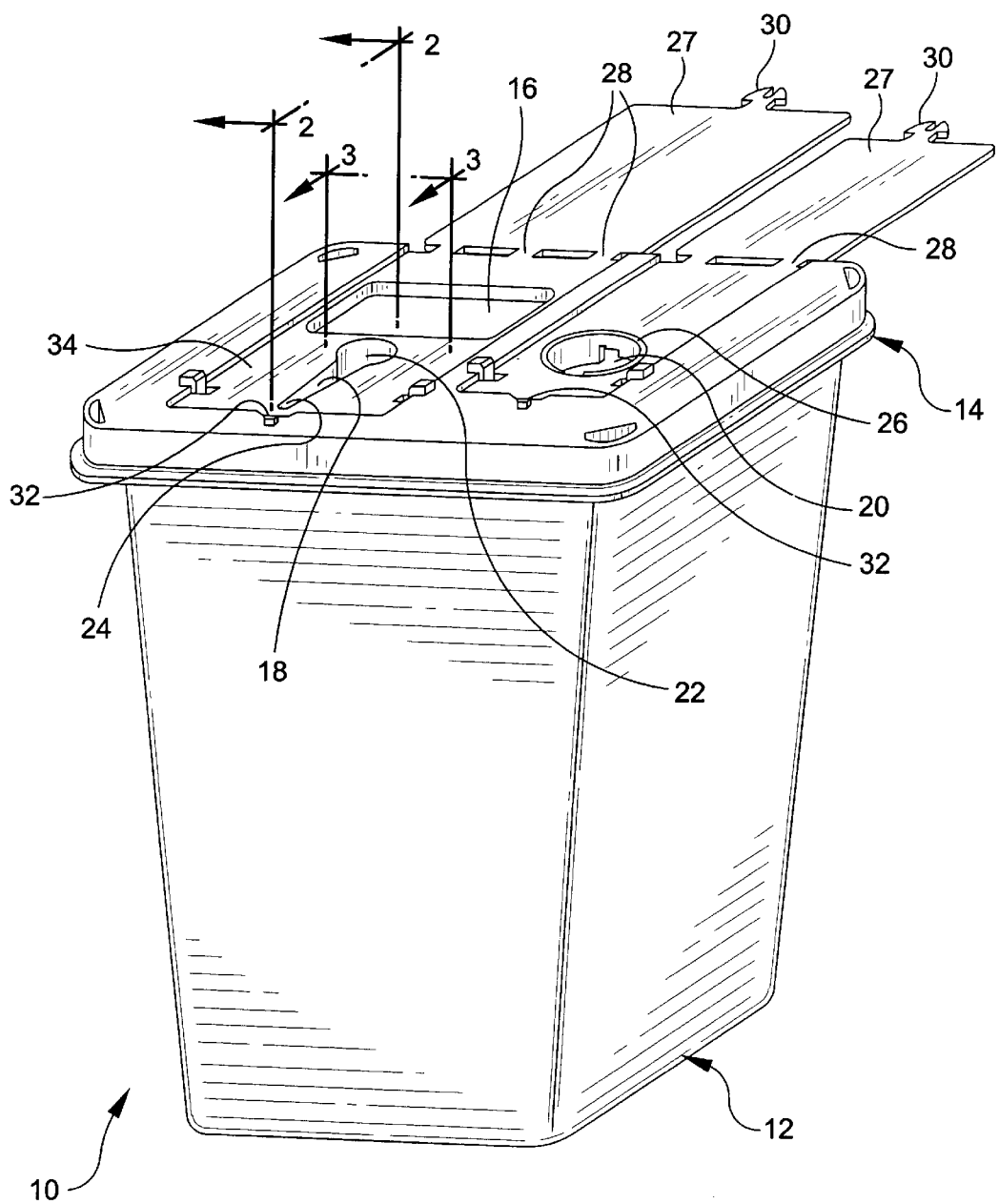
FIG. 1 is a perspective view of the sharps disposal assembly of the invention with the lid closure flaps open.

Adverting now to the drawings, wherein like elements are given the same reference number followed by a lower case letter in the various illustrations thereof, FIG. 1 illustrates a sharps disposal assembly 10 including a receptacle 12 and a lid 14. Lid 14 has a large port opening 16, a slot opening 18 tapered to form a "V" and a circular opening 20. Port opening 16 may be of any suitable geometrical configuration, but for purpose of illustration is shown in the preferred rectangular shape. Tapered slot opening 18 extends from large end 22 to narrow end 24 wherein large end 22 is of sufficient size to accept a needle shield, and thus may preferably be about 10–15 mm across. Alternatively, the port and slot openings may be combined into single continuous opening. Circular opening 20 in lid 14 has insert 26 therein expressly dimensioned to engage a SAFETY-GARD™ tube holder, as sold by Becton, Dickinson and Company. Opening 20 and insert 26 are conventional features of prior art sharps disposal receptacles and are fully described in the aforementioned U.S. Pat. No. 5,092,462.

Flaps 27 are affixed to lid 14 by integral tabs 28 and have integral closure tabs 30 dimensioned for insertion into slots 32 of a plate portion 34 of lid 14 to cover the openings.

Figure 2:
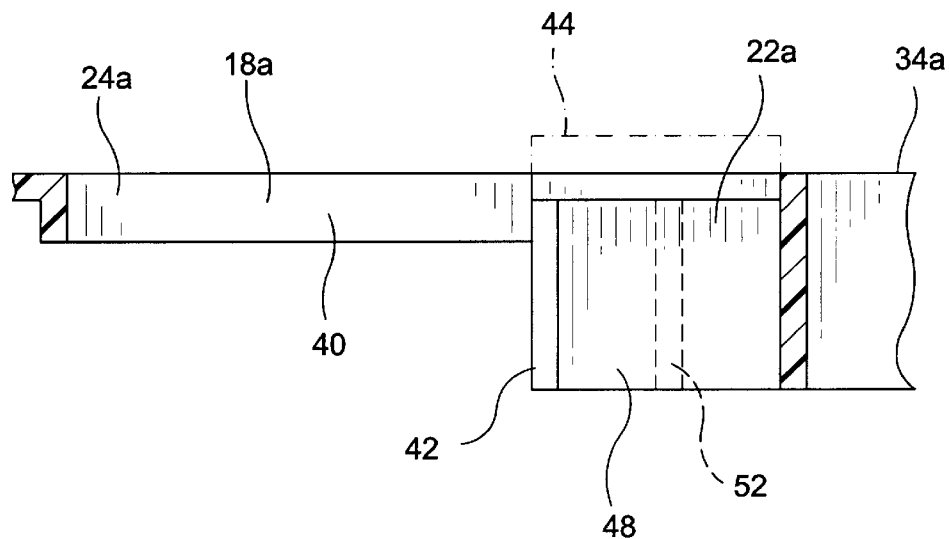
FIGS. 2 and 3 are transverse and longitudinal cross-sectional views taken along the lines 2—2 and 3—3 respectively of the assembly of FIG. 1 illustrating details of the unwinder.
Figure 3:
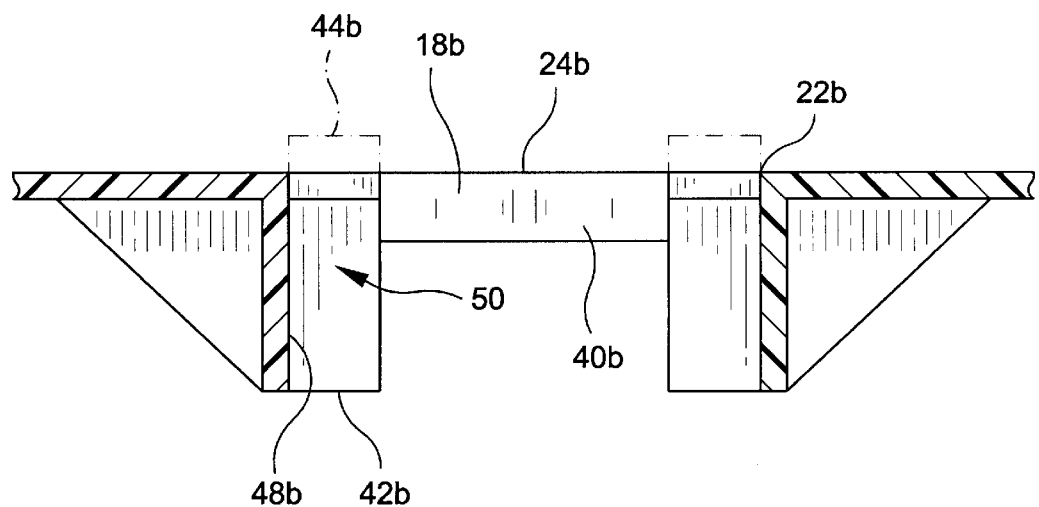

FIGS. 2 and 3 illustrate slot opening 18a to be bounded by an edge or wall 40. Edge 40 abuts a post flange 42 which depends perpendicularly downward from edge 40. A wedge flange 44 (shown in phantom) is an integral segment of a plate portion 34a of lid 14a. A substantially square wall flange 48 extends under wedge flange 44 and meets post flange 42 at a right angle. As best seen in FIG. 3, the underside of wedge flange 44b, post flange 42b and wall flange 48b define a recess 50, which, together with a corresponding recess formed by the post, wall and wedge flanges on the other side of the slot opening, form a substantially cubical compartment for receiving a needle shield, as described below. Also shown in phantom in FIG. 2 is an optional support rib 52 extending from the back side of wall flange 48 to the underside of plate 34b to add rigidity to flange 48.

Figure 4:
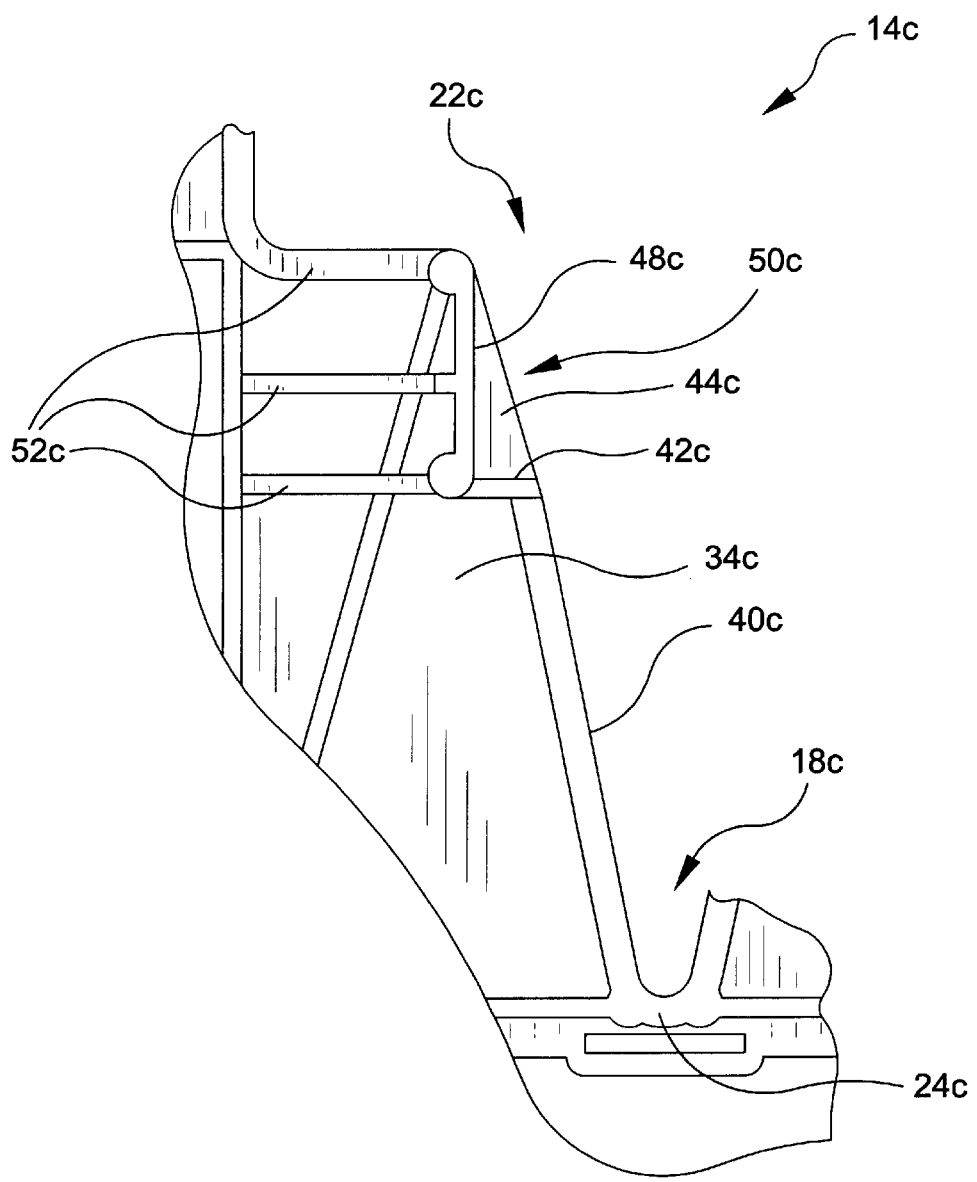
FIG. 4 is a transverse cross-sectional view of the assembly of the invention taken along the line 2—2 thereof and viewed from the underside of the unwinder.

In FIG. 4, the relationship of post flange 42c, wedge flange 44c and wall flange 48c to give recess 50c is shown as viewed toward the underside of lid 14c. FIG. 4 also shows support ribs 52c to be integral with plate 34c.

Figure 5:
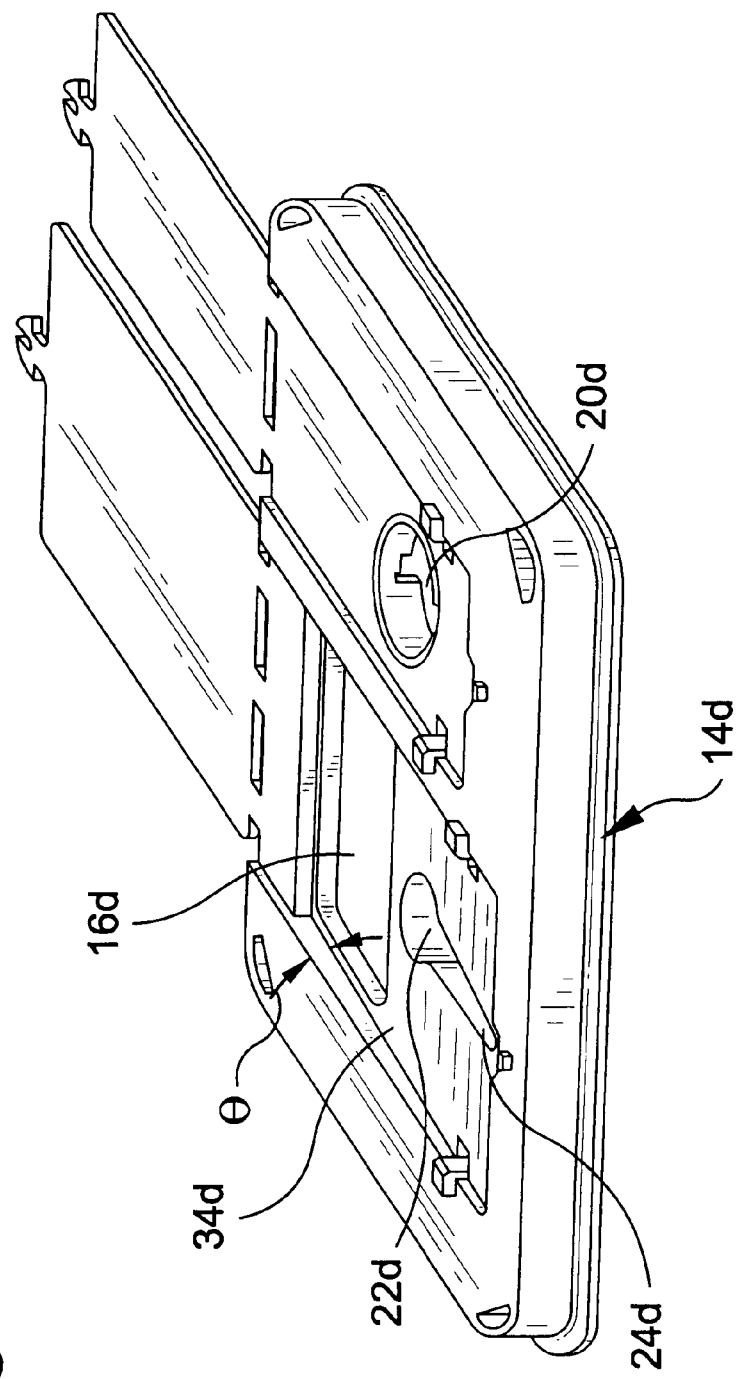
FIG. 5 is a side elevational view of an alternative embodiment of the invention.

In another embodiment of the invention, illustrated in FIG. 5, plate 34d may be sloped at an angle theta from the plane of lid 14d. Angle theta may be about 5–20°, preferably 10–15°, so that narrow unwinder end 24d is higher than large end 22d. This configuration causes a needle-hub unit, after unwinding, to slide down the slope and thereby aids in overcoming hangup.

Figure 6:
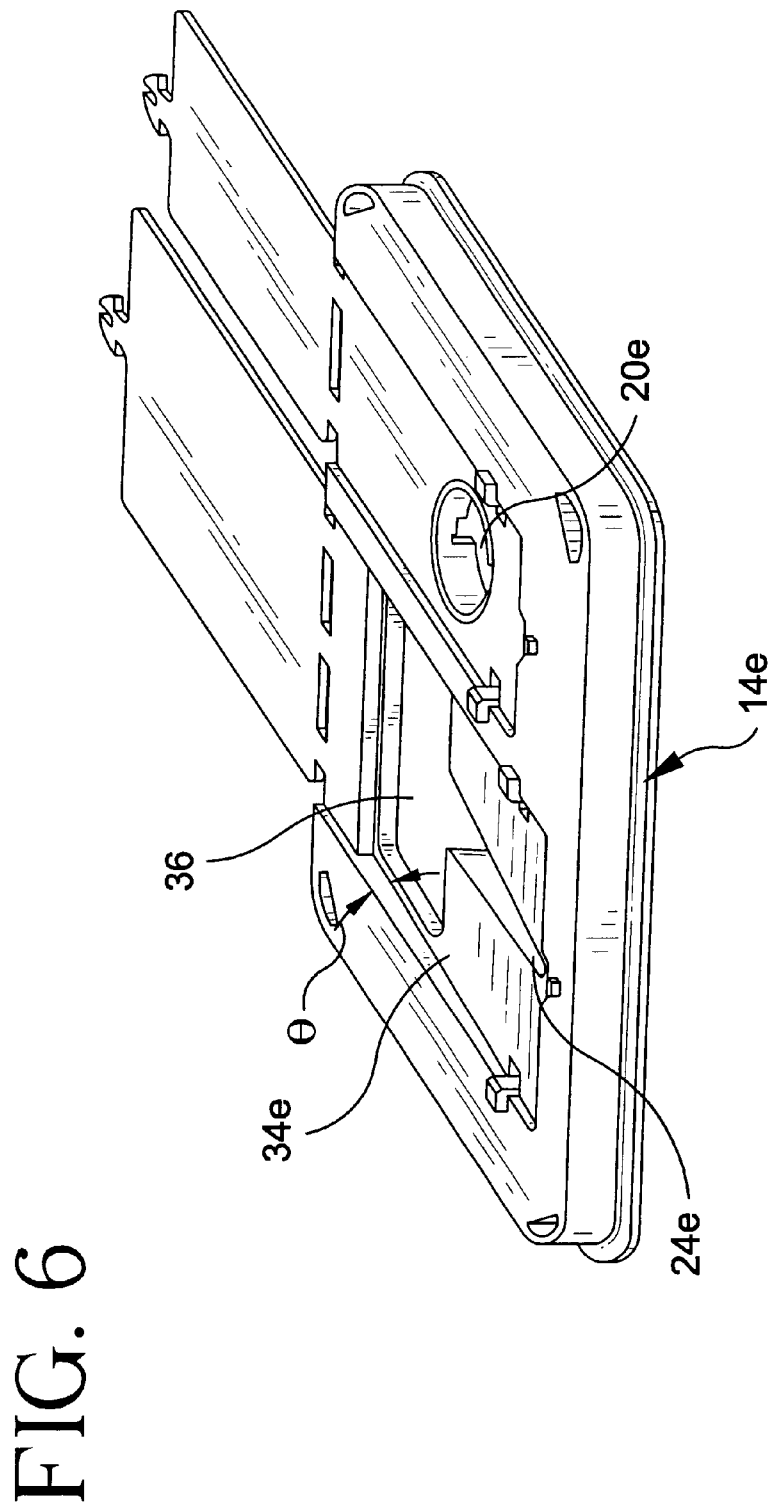
FIG. 6 is a side elevational view of an alternate embodiment of the invention.

In still another embodiment of the invention, illustrated in FIG. 6, the port and slot openings are combined into a single continuous opening 36.

The new unwinder design of the invention greatly improves reliability and user safety in disposal of needles protected by needle shields. In use, the technician, grasping the needle holder, inserts the used needle shield unit into the large end of the slot opening with the top of the shield collar aligned slightly below the lid plate. The shield may then be advanced with any of its four faces, front, back, left or right, leading into the compartment formed by the three flanges until the technician feels contact of the shield with the post flange. At this point, the shield is properly positioned in the compartment by a loose fit, without touching any of the flanges, i.e., the compartment is dimensioned so that spaces are present along all sides of the shield. This design thus provides six areas of support from the flanges during twisting for effortless unwinding and assured drop into the receptacle because substantially all problems of hangup are overcome.

The assembly of the invention may be made of any suitable plastic, such as polyethylene, polypropylene and polyvinyl chloride. The lid with the unwinder elements is preferably made by conventional injection molding with integral construction wherein all of the parts are continuous with no seams therebetween.

What is claimed is:

1. An assembly for receiving and disposing of a needle-hub-safety shield unit comprising:
   a) a substantially rigid storage receptacle;
   b) a lid for said receptacle comprising plate portion defining a plurality of openings into said receptacle;
   c) edge circumscribing a first of said openings, said first opening for unwinding a needle-hub-safety shield unit;
   d) a plurality of flanges depending from said plate portion and defining a compartment for receiving and immobilizing said needle-hub-safety shield unit against twisting and ascending motion during said unwinding, a first of said flanges being a wedge segment of said plate portion and a second of said flanges being a wall of said compartment, said wall being perpendicular to and under said wedge flange and a support rib for said wall.

2. The assembly of claim 1 wherein a third of said flanges is a post flange downwardly depending and perpendicular to said plate portion.

3. The assembly of claim 1 wherein a second of said openings is substantially rectangular and dimensioned to receive a large medical article.

4. The assembly of claim 1 wherein said plate portion is sloped at an angle to said lid.

5. The assembly of claim 3 wherein a third of said openings is annular in shape and contains an insert therein to engage a needle holder.

6. The assembly of claim 5 wherein said lid further comprises flap means for covering said openings, said flap means including locking means for affixing said flap means to said lid over said openings.

7. An assembly for receiving and disposing of a needle-hub-safety shield unit comprising:
   a) substantially rigid storage receptacle;
   b) a lid for said receptacle, said lid including a substantially flat plate portion defining a plurality of openings, said plate portion being sloped at an angle to said lid, a first of said openings being a substantially V-shaped unwinder opening circumscribed by an edge and a second of said openings being a substantially rectangular port opening;
   c) a post flange depending downwardly from said plate portion;
   d) a wall flange depending downwardly from said plate portion, said wall flange being perpendicular to said post flange and to said plate portion;
   e) a wedge flange comprising a segment of said plate portion and being bounded by said post and wall flanges, said post, wall and wedge flanges defining a compartment for receiving and immobilizing a needle-hub-safety shield unit;
   f) a support rib integral with said plate portion and said wall flange; and
   g) a flap affixed to said lid for covering at least one of said openings.

8. The assembly of claim 3 wherein said first and second openings are combined into a single continuous opening.

* * * * *